(12) United States Patent
Li et al.

(10) Patent No.: US 9,365,816 B2
(45) Date of Patent: Jun. 14, 2016

(54) HANDHELD LOW PRESSURE MECHANICAL CELL LYSIS DEVICE WITH SINGLE CELL RESOLUTION

(75) Inventors: Zhenyu Li, McLean, VA (US); Axel Scherer, Woodstock, VT (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 986 days.

(21) Appl. No.: 13/230,933

(22) Filed: Sep. 13, 2011

(65) Prior Publication Data

US 2012/0091235 A1   Apr. 19, 2012

Related U.S. Application Data

(60) Provisional application No. 61/382,434, filed on Sep. 13, 2010.

(51) Int. Cl.
*B01L 3/00* (2006.01)
*C12M 1/00* (2006.01)
*C12N 1/06* (2006.01)

(52) U.S. Cl.
CPC ............... *C12M 47/06* (2013.01); *C12N 1/066* (2013.01)

(58) Field of Classification Search
None
See application file for complete search history.

(56) References Cited

U.S. PATENT DOCUMENTS

| 5,635,358 | A  | * | 6/1997  | Wilding et al. ............... 435/7.2 |
| 8,002,235 | B2 |   | 8/2011  | Vyawahare et al. |
| 2004/0224380 | A1 | * | 11/2004 | Chou et al. ..................... 435/29 |
| 2008/0274493 | A1 |   | 11/2008 | Quake et al. |
| 2009/0098541 | A1 |   | 4/2009  | Southern et al. |
| 2009/0152110 | A1 | * | 6/2009  | Hiraoka et al. .......... 204/403.01 |
| 2010/0068781 | A1 |   | 3/2010  | Rajagopal et al. |
| 2013/0209988 | A1 |   | 8/2013  | Barber et al. |

OTHER PUBLICATIONS

Zhong, J.F. et al. "A microfluidic processor for gene expression profiling of single human embryonic stem cells" *Lab Chip* Jan. 2008 8(1): pp. 68-74.

(Continued)

*Primary Examiner* — Natalia Levkovich
(74) *Attorney, Agent, or Firm* — Steinfl & Bruno LLP

(57) ABSTRACT

Apparatus and methods for mechanical cell lysis with single cell resolution which requires very low applied pressure. The device can be handheld, simple to operate, requires no external power except for hand-applied pressure via a syringe, and is applicable to all cell types including yeast and bacterial cells. The device is also capable of mechanically lysing a single cell. A single cell is selected from a biological sample of interest. The single cell is lysed by application of mechanical stress in a single cell lysing apparatus having a trap structure for deterministically capturing the cell and a stress raiser that cooperates with a source of mechanical stress so as to apply sufficient force to rupture a cell. The stress raiser can be a properly designed edge of the trap or it can be a lithographically produced structure such as a nanoblade or a nanopillar.

20 Claims, 6 Drawing Sheets

(56) References Cited

OTHER PUBLICATIONS

Tan, W-H. et al. "A trap-and-release integrated microfluidic system for dynamic microarray applications" *PNAS* Jan. 23, 2007, vol. 104, No. 4, pp. 1146-1151.

Ahmad, M.R. et al. "In Situ Single Cell Mechanics Characterization of Yeast Cells Using Nanoneedles Inside Environmental SEM" *IEEE Transactions on Nanotechnology* vol. 7, No. 5, Sep. 2008, pp. 607-616.

Henry, M.D. et al. "Alumica etch masks for fabrication of high-aspect-ratio silicon micropillars and nanopillars" *Nanotechnology* 20 (2009) pp. 1-4.

de Boer, M.J. et al. "Guidelines for Etching Silicon MEMS Structures Using Fluorine High-Density Plasmas at Cryogenic Temperatures" *Journal of Microelectromechanical Systems*, vol. 11, No. 4, Aug. 2002, pp. 385-401.

Welch, C.C. et al. "Silicon etch process options for micro- and nanotechnology using inductively coupled plasmas" *Microelectronic Engineering* 83 (2006) pp. 1170-1173.

Brown R. et al. "Current techniques for single-cell lysis" *J. R. Soc. Interface* (2008) 5, pp. S131-S138.

International Search Report mailed on May 21, 2012 for PCT/US2011/051298 filed on Sep. 13, 2011 California Institute of Technology et al.

Written Opinion mailed on May 21, 2012 for PCT/US2011/051298 filed on Sep. 13, 2011 California Institute of Technology et al.

\* cited by examiner

FIG. 1A       FIG. 1B       FIG. 1C
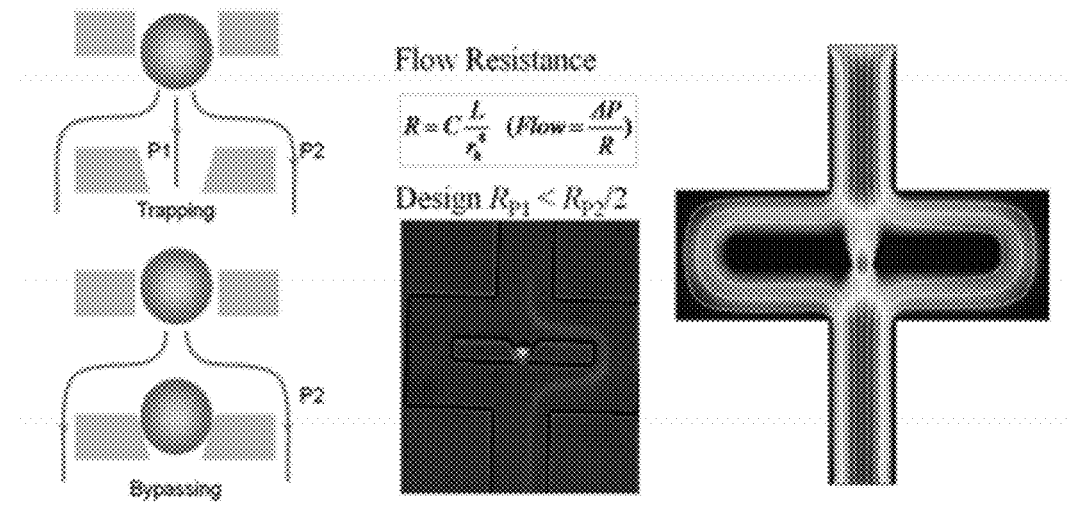
HeLa Cell
< 4 psi
FIG. 1D
*C. Elegan* Egg
< 15 psi
FIG. 1E
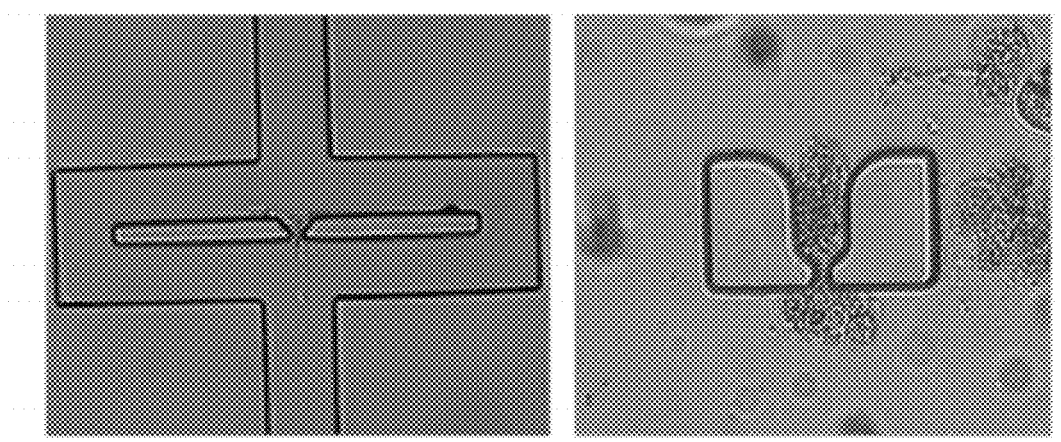

FIG. 2A
FIG. 2C
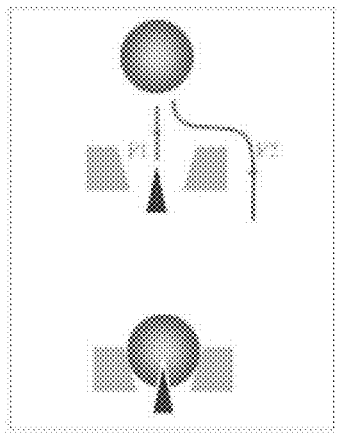
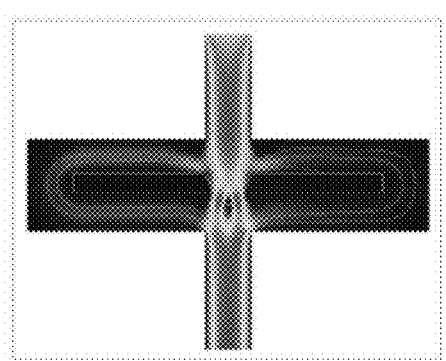
Finite Element Simulation
FIG. 2B
FIG. 3B
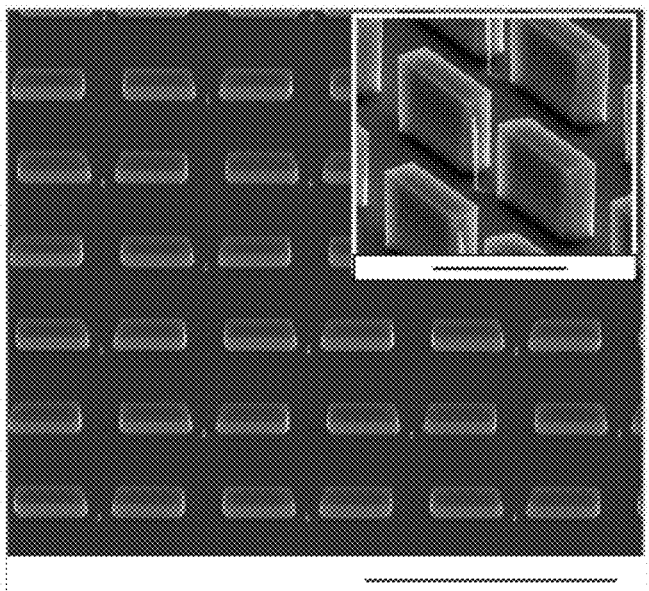
- Needed for disrupting yeast cells and bacterial cells
  - ~1000Psi local pressure is needed
- Sub 50nm Nanoblades on Silicon chip can generate >2000Psi local pressure from 40Psi applied pressure
- Suitable as a handheld device
  - Hand press a 3cc plastic syringe can generate >50Psi pressure
FIG. 3A FIG. 5A
PRIOR ART
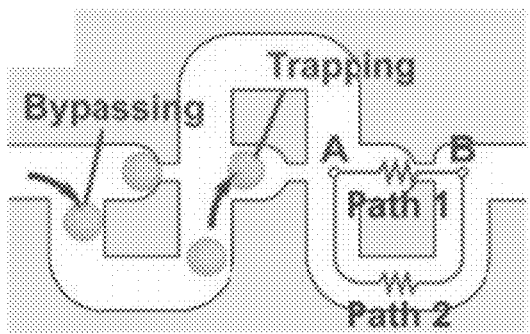
FIG. 5B
PRIOR ART
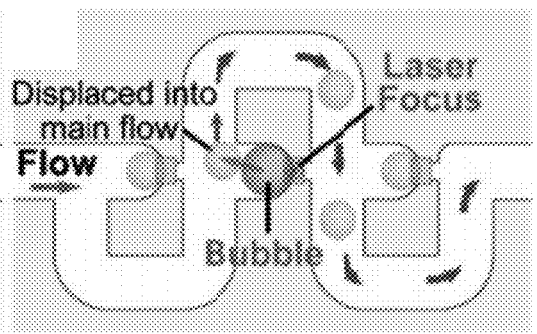
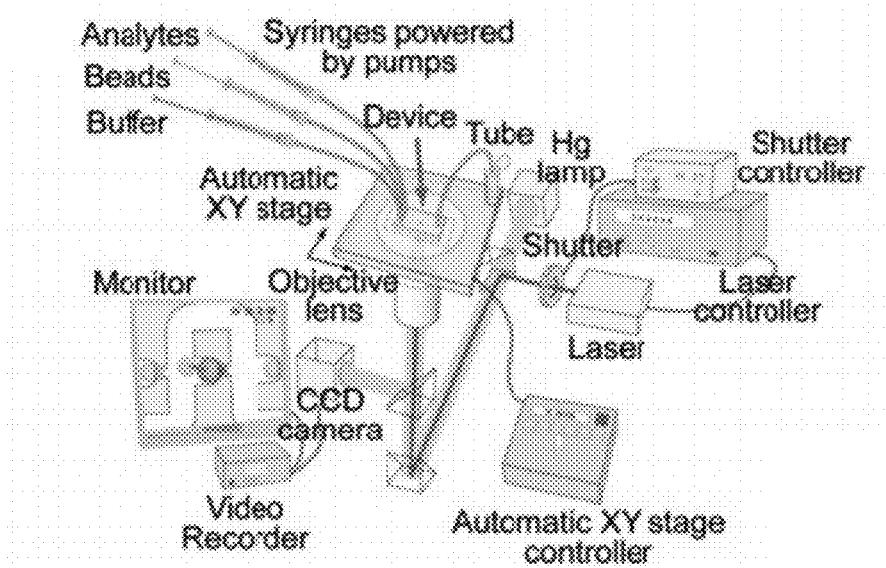
FIG. 5C
PRIOR ART

HANDHELD LOW PRESSURE MECHANICAL CELL LYSIS DEVICE WITH SINGLE CELL RESOLUTION

CROSS-REFERENCE TO RELATED APPLICATIONS

This application claims priority to and the benefit of U.S. provisional patent application Ser. No. 61/382,434 filed Sep. 13, 2010, which application is incorporated herein by reference in its entirety.

FIELD OF THE INVENTION

The invention relates to processing biological materials in general and particularly to a system and method that employs mechanical lysing of cells.

BACKGROUND OF THE INVENTION

Cell disruption, or lysis, is the first step in the extraction of nuclear acid, protein and other subcellular components from biological cells used in many biochemical and molecular analysis assays such as polymerase chain reaction (PCR). Cell lysis can be accomplished by either physical or chemical approaches. Chemical approaches use enzymes or detergents to dissolve cell members or walls. Physical approaches include the use of high speed blenders, high pressure liquid homogenizers, a French press, bead beating, sonication, freeze/thaw and grinding with a mortar and pestle. Among these methods, high-shear mechanical lysis such as French press is often the method of choice especially for breaking bacterial and yeast cells, and when enzymatic and detergent approaches are not compatible with subsequent processing steps. However, traditional high-shear mechanical cell lysis equipment require extremely high operating pressure (up to 40,000 psi) and the heating due to high power dissipation often leads to the denaturation of desired biomolecules. Moreover, such bulky, expensive and complex equipment cannot be used in portable devices for point-of-care diagnostics, environmental monitoring and pathogen detection.

Jiang F. Zhong, et al., "A microfluidic processor for gene expression profiling of single human embryonic stem cells," Lab Chip, 2008, 8, 68-74, is a paper that demonstrates that the observed gene expression for a single human embryonic stem cell (hESC) is different than the gene expression observed for a plurality of hESC taken from the same individual. The paper suggests that heterogeneity of the mammalian cell populations may be a factor related to the observed expression variations in single-cell analysis of mammalian cells. The paper indicates that "[w]hen gene expression studies are conducted at the single-cell level, we must recognize that no two cells are identical." Some of the reasons why this should be so include the variability in such factors as differences in cell cycle, differentiation stages, and environmental stimulation for different cells in a particular cell population. For a particular cell population, there can be variation of gene expression at the single-cell level, which may be due to stochastic expression fluctuation, or due to heterogeneity of the cell populations. In the procedures described in this paper, cells were chemically lysed, and their DNA and RNA contents were studied in a microfluidic system.

Existing mechanical cell lysis equipment do not have single cell lysis resolution which is required for single cell biological studies that are increasingly used in stem cell, embryonic development and cancer research due to the intrinsic heterogeneity in such cell populations.

There is a need for systems and methods that provide the ability to lyse individual cells under carefully controlled conditions.

SUMMARY OF THE INVENTION

According to one aspect, the invention features a mechanical cell lysing apparatus with single cell resolution. The apparatus comprises an inlet port configured to permit a cell of interest to enter the mechanical single cell lysing apparatus; a trap structure configured to trap the cell of interest in the single cell lysing apparatus; a stress raiser configured to raise a mechanical stress on a membrane of the cell of interest trapped in the trap structure; a pressure application element configured to apply a pressure to the cell of interest, the pressure application element configured to cooperate with the stress raiser to provide sufficient mechanical stress to lyse the cell of interest trapped in the trap structure; and an outlet port configured to allow components of the lysed cell of interest to exit the mechanical single cell lysing apparatus to be analyzed.

In one embodiment, the stress raiser is an edge of the trap structure.

In another embodiment, the stress raiser is a nanoblade.

In yet another embodiment, the stress raiser is a nanopillar.

In still another embodiment, the pressure application element is a manually operated pressure application element.

In a further embodiment, the pressure application element is an electrically operated pressure application element.

In yet a further embodiment, the electrically operated pressure application element is configured to be controlled by a computer.

In an additional embodiment, a flow condition of at least one of the inlet port and the outlet port is controlled by a valve.

In one more embodiment, the apparatus comprises a selected one of silicon, glass, quartz, polymer and metal material.

In one embodiment, the apparatus is configured as a handheld device.

According to another aspect, the invention relates to a mechanical cell lysing method with single cell resolution. The mechanical single cell lysing method comprises the steps of providing a mechanical single cell lysing apparatus; providing a biological material of interest; selecting a single cell to be lysed; introducing the single cell to be lysed into the mechanical single cell lysing apparatus; applying sufficient pressure to mechanically lyse the single cell; and providing components of the mechanically lysed single cell for analysis. The mechanical single cell lysing apparatus comprises an inlet port configured to permit a cell of interest to enter the mechanical single cell lysing apparatus; a trap structure configured to trap the cell of interest in the single cell lysing apparatus; a stress raiser configured to raise a mechanical stress on a membrane of the cell of interest trapped in the trap structure; a pressure application element configured to apply a pressure to the cell of interest, the pressure application element configured to cooperate with the stress raiser to provide sufficient mechanical stress to lyse the cell of interest trapped in the trap structure; and an outlet port configured to allow components of the lysed cell of interest to exit the mechanical single cell lysing apparatus to be analyzed.

In one embodiment, the step of applying sufficient pressure to mechanically lyse the single cell is performed manually.

In another embodiment, the step of applying sufficient pressure to mechanically lyse the single cell is performed electrically.

In yet another embodiment, the step of selecting a single cell to be lysed is performed using a trap and release apparatus.

In still another embodiment, the step of selecting a single cell to be lysed is performed using a visual method of identification of the cell.

In a further embodiment, the visual method of identification of the cell comprises, but is not limited to, staining the cell, fluorescence in situ hybridization (FISH), fluorescent protein transfection, or Raman spectrum.

In yet a further embodiment, the step of selecting a single cell to be lysed is performed manually.

In an additional embodiment, the method further comprises the steps of analyzing a component of the lysed cell and reporting a result of said analysis.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 1A is a diagram that illustrates a trapping mechanism.

FIG. 1B is an optical micrograph showing a fluorescently labeled HeLa cell (diameter ~12 um) trapped in a real device and a second cell bypassing the trap thus avoiding clogging the channel.

FIG. 1C is a diagram showing the result of a finite element simulation that illustrates the streamline and velocity field. The higher velocity at the center of the trap verifies that P1 has a lower flow resistance than P2.

FIG. 1D is a micrograph showing the shear force lysis of HeLa cells at 4 psi pressure by thumb pressing a 3 cc syringe.

FIG. 1E is a micrograph showing the shear force lysis of round worm C. elegan eggs at 15 psi pressure by thumb pressing a 3 cc syringe.

FIG. 2A and FIG. 2B are schematic diagrams showing the principle of hydrodynamic routing of cells to predefined locations where nanoblades generate high enough local pressure to break cell walls.

FIG. 2C is a diagram showing a finite element simulation of the flow regime.

FIG. 3A is a scanning electron microscope image of a cell lysis device based on hydrodynamic routing and nanoblades.

FIG. 3B is an inset diagram showing an enlarged view of a portion of the structure in FIG. 3A.

FIG. 5A is a plan schematic diagram of a prior art microfluidic trap.

FIG. 5B is a diagram illustrating a release mechanism using a microbubble.

FIG. 5C is a perspective diagram illustrating a prior art apparatus used to operate the traps of FIG. 5A.

DETAILED DESCRIPTION

Figure 4:
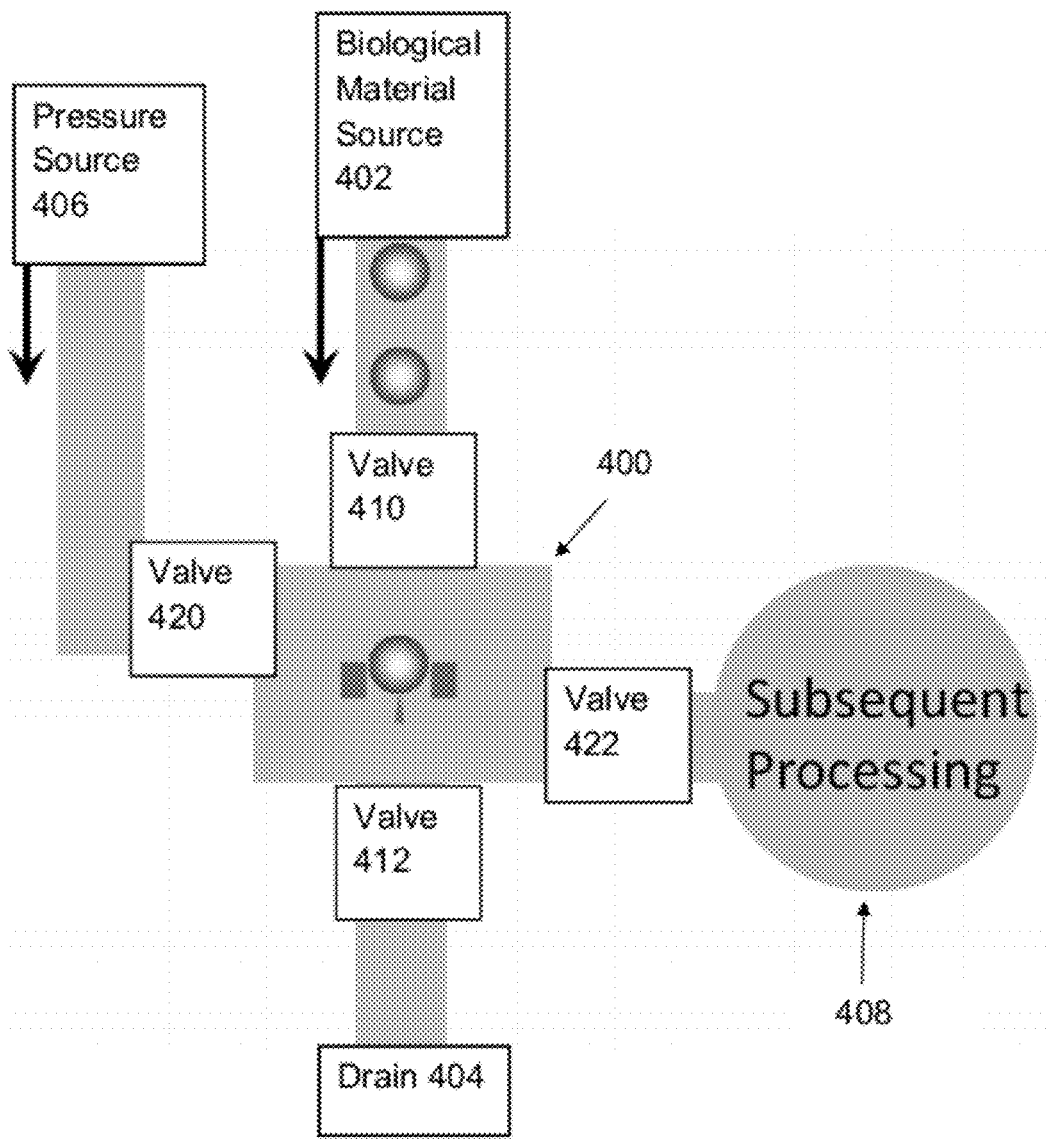
FIG. 4 is a schematic diagram of a single cell lysis device.

This invention provides a handheld mechanical cell lysis device with single cell resolution which requires very low applied pressure (less than 5 psi for mammalian cells, less than 40 psi for yeast cells). The device is small, simple to operate, requires no external power except for hand-applied pressure via a syringe, and is applicable to all cell types including yeast and bacterial cells. The operation of the device is based on low Reynolds number hydrodynamic flow which can deterministically route cells to predefined locations on a microfluidic chip where shear force or local pressure is high enough to rupture the cells. Enough shear force to cause a cell membrane to rupture under modest externally applied force can be attained by providing a structure comprising a stress raiser. Two mechanisms are used to generate high enough forces to break cell membranes or cell walls on-chip. In the first approach, by simply narrowing the flow channel width at predefined lysis positions, sufficient shear stress is generated to break mammalian cell membranes. In the second approach, nanoscale blades are provided in the middle of the lysis positions to amplify the local pressure so that harder cell walls found in yeast and bacterial cells can be broken. This mechanical cell lysis device is expected to find applications in sample preparation for point-of-care diagnostics, pathogen detection and routine biomedical laboratory operations that deal with small sample volumes. Furthermore, when combined with on-chip microfluidic valves, this single cell lysis device can offer selective single cell lysis function for the extraction of DNA, RNA and proteins from a specific single cell, a prerequisite for the molecular and biochemical studies of single embryo, tumor and stem cells.

Hydrodynamic Trapping and Subsequent Lysis of Mammalian Cells by Shear Force

The first approach uses the hydrodynamic trapping method demonstrated by Tan et al. (discussed in further detail below) to first deterministically trap individual cells at predefined locations in a microfluidic channel. The microfluidic channel can be made of silicon, quartz, glass, polymer or metal material by using conventional photolithography, dry/wet etching, molding, imprint or hot embossing techniques.

FIG. 1A is a diagram that illustrates the trapping mechanism. At the top of FIG. 1A an empty trap captures a single cell because path P1 is designed to have a lower flow resistance than path P2. At the bottom of FIG. 1A a filled trap diverts subsequent cells to path P2 (also referred to as "bypassing").

FIG. 1B is an optical micrograph showing a fluorescently labeled HeLa cell (diameter ~12 um) trapped in a real device and a second cell bypassing the trap on the right hand side thus avoiding clogging the channel.

FIG. 1C is a diagram showing the result of a finite element simulation that illustrates the streamline and velocity field. The higher velocity at the center of the trap verifies that P1 has a lower flow resistance than P2.

Each trap in FIG. 1A is a V-shaped groove structure with a small opening at the center. The size of the opening is smaller than the diameter of the cell of interest. The trap geometry is designed such that when a trap is empty the trapping path P1 through the opening has a lower flow resistance than the bypassing path P2. The flow resistance of a given path can be expressed as:

$$R = C \frac{L}{r_h^4}$$

where C is a constant determined by the channel geometry and liquid properties, L is the channel length, and $r_h$ is the hydrodynamic radius of the channel. We can design L and $r_h$ so that $R_{P1}$ is much smaller than $R_{P2}$. Therefore a cell in the flow will prefer to go into an empty trap. However when a trap captures a cell, the flow resistance of P1 will increase dramatically and subsequent cells will be diverted to follow lower resistant path P2 bypassing the filled trap. As shown in FIG. 1B (lower middle), a fluorescent labeled HeLa human tumor cell has been successfully trapped and a subsequent cell' is bypassing the trap without clogging the channel.

Once the cell is trapped at the V-shaped groove, which is designed to provide a stress raiser at the trap location, increasing the applied pressure can generate high enough shear force to pull apart the cell membrane and release the cellular content as shown in FIG. 1D. FIG. 1D is a micrograph showing the shear force lysis of HeLa human tumor cells at 4 psi pressure by thumb pressing a 3 cc syringe. C. elegan eggs have stronger three-layered shells. FIG. 1E is a micrograph showing the shear force lysis of round worm C. elegan eggs at 15 psi pressure by thumb pressing a 3 cc syringe.

Hydrodynamic Routing and Subsequent Lysis of Cells with Cell Wall by High Local Pressure Generated by Nanoblades In order to break harder cells such as bacterial and yeast cells, higher pressure is needed than that can be generated in the first approach. Yeast cell walls typically require 1000-2000 psi local pressure to break as demonstrated in cell mechanical studies using nanoneedles (see M. R. Ahmad, et al, "In Situ Single Cell Mechanics Characterization of Yeast Cells Using Nanoneedles Inside Environmental SEM", IEEE TRANSACTIONS ON NANOTECHNOLOGY, VOL. 7, NO. 5, 607-616, SEPTEMBER 2008). Such high local pressure can be generated from a much lower applied pressure if the applied force can be concentrated on a small area on the cell wall by forcing the cell onto a stress raiser such as a nanoblade or a nanoneedle.

FIG. 2A and FIG. 2B are schematic diagrams showing the principle of hydrodynamic routing of cells to predefined locations where a stress raiser provided by a nanoblade generates high enough local pressure to break cell walls. High velocity around the nanoblade in path P1 shows that P1 still has lower flow resistance than that of P2 so that the flow will deterministically direct cells to the nanoblade locations for high efficient cell lysis without causing channel clogging. The amplification ratio of local pressure to applied pressure is given by the ratio of the cell cross-sectional area to the nanoblade tip area in contact with the cell wall.

FIG. 2C is a diagram showing a finite element simulation of the flow regime.

Modern fabrication techniques such as deep ultraviolet (DUV) photolithography or electron beam (e-beam) lithography combined with nonisotropic dry etching can routinely define sub 50 nm features on silicon that have a high aspect ratio. An example of a cell lysis device with nanofabricated nanoblades is shown in FIG. 3A and FIG. 3B are.

FIG. 3A is a scanning electron microscope image of a cell lysis device based on hydrodynamic routing and nanoblades. In FIG. 3A the scale line is 100 microns long. The high local pressure generated by the nanoblades can break open cell walls of yeast and bacterial cells.

FIG. 3B is an inset diagram showing an enlarged view of a portion of the structure in FIG. 3A. In FIG. 3B the scale line is 30 microns long.

A Single Cell Lysis Device

FIG. 4 is a schematic diagram of a single cell lysis device 400 that operates based on the second approach using a nanoblade. A source of biological material 402 is provided that communicates with the single cell lysis device 400 by way of a valve 410. With valves 410 and 412 open and valves 420 and 422 closed, biological material of interest, such as a human cell, a bacterium, or some other cell, is provided to the single cell lysis device 400. Excess material is allowed to leave the single cell lysis device 400 by way of valve 412 to a drain 404. When valves 420 & 422 are closed, a cell is trapped above the nanoblade by hydrodynamic routing. Next, valves 410 and 412 are closed to isolate the trapped cell. Then valve 420 is opened and pressure is applied by pressure source 406 to mechanically lyse the cell. In some embodiments, pressure source 406 is a manually applied source of pressure. In other embodiment, pressure source 406 is a machine-based pressure source. After the cell of interest has been lysed, valve 422 is opened and cell lysate is flushed out for subsequent processing, denoted by 408.

Traping and Releasing Cells

FIG. 5 illustrates one example of a method and an apparatus for trapping individual microbeads, which can be decorated with a biological material, including cells, is described in Wei-Heong Tan and Shoji Takeuchi, "A trap-and-release integrated microfluidic system for dynamic microarray applications," PNAS, Jan. 23, 2007, vol. 104, no. 4, pp. 1146-1151.

This paper describes one example of a system and methods that can be used to trap and recover individual microbeads. A microbead can have attached to it a material of biological interest, including a cell. Using this system, or other systems that allow a single cell of interest to be separated from a group of cells and further manipulated, a single cell can be made available for lysing and further examination.

The system is based on microfluidic technology using a design that has a straight channel with a one or more traps connected to channels that form side loops around segments of the straight channel, and relies on the principle that fluidic resistance along the straight channel is smaller, and beads in the flow will be carried into the trap; but once the traps are filled, the flow will be redirected to the loop channels.

FIG. 5A is a plan schematic diagram of a microfluidic trap. When the trap is empty, flow resistance along the straight channel is lower than that of the loop channel, and the main stream flows along the straight channel. A bead in the flow is carried by the main stream into the trap if it is empty (trapping mode). Beads will be carried along the loop channel if the trap is filled, bypassing the occupied trap (bypassing mode). This design allows for one-bead-to-one-trap. It comprises squarewave shaped loop channels superimposed onto a straight channel, with narrowed regions along the straight channel functioning as traps. The channels are designed such that when a trap is empty, the straight channel has a lower flow resistance than that of the loop channel. As a result, we have bulk of the fluid flowing along the straight channel. A particle in the flow will be carried by this main stream into the trap (trapping mode). This particle acts as a plug, increasing the flow resistance drastically along the straight channel, and redirecting the main flow to the loop channel. Subsequent particles will then be carried along the loop channel, bypassing the filled trap (bypassing mode). Based on a simple model, the design criterion for this trap is derived.

Pressure Drop in a Microchannel

Tan et al. (or alternatively, "Tan") used the Darcy-Weisbach equation to determine the pressure drop or pressure difference in a microchannel. They solved the continuity and momentum equations for the Hagen-Poiseuille flow problem to obtain the pressure difference $$\Delta p = fL\rho V^2/2D,$$

where f is the Darcy friction factor, L is the length of the channel, $\rho$ is the fluid density, V is the average velocity of the fluid, and D is the hydraulic diameter, respectively. D can be further expressed as 4A/P for a rectangular channel, and V as Q/A, where A and P are the cross-sectional area and perimeter of the channel, and Q is the volumetric flow rate. The Darcy friction factor, f, is related to aspect ratio, $\alpha$, and Reynolds number, $Re = \rho V D/\mu$, where $\mu$ is the fluid viscosity. The aspect ratio is defined as either height/width or width/height such that $0 \leq \alpha \leq 1$. The product of the Darcy friction factor and Reynolds number is a constant that depends on the aspect ratio, i.e., $f \times Re = C(\alpha)$, where $C(\alpha)$ denotes a constant that is a function of $\alpha$. After simplifications, one obtains the expression $$\Delta p = \frac{C(\alpha)}{32} \cdot \frac{\mu L Q P^2}{A^3}. \qquad \text{Eqn (1)}$$

Design Criterion for a Microfluidic Trap

In FIG. 5A, we have the simplified circuit diagram of the trap. Fluid can flow from junction A to B via path 1 or 2. Ignoring minor losses due to bends, widening/narrowing, etc., Eqn. (1) is applied separately for paths 1 and 2, and because the pressure drop is the same for both paths, one equates both expressions to yield $$\frac{Q_1}{Q_2} = \left(\frac{C_2(\alpha_2)}{C_1(\alpha_1)}\right) \cdot \left(\frac{L_2}{L_1}\right) \cdot \left(\frac{P_2}{P_1}\right)^2 \cdot \left(\frac{A_1}{A_2}\right)^3, \qquad \text{Eqn (2)}$$

where subscripts 1 and 2 denote paths 1 and 2, respectively. For path 1, the length, L1, is assumed to be that of the narrow channel to simplify analysis. This is valid because most of the pressure drop occurs along the narrow channel. For the trap to work, the volumetric flow rate along path 1 must be greater than that of path 2, i.e., Q1>Q2. Using the relationships $A = W \times H$ and $P = 2(W+H)$, where H is the height of the channels, one derives $$\left(\frac{C_2(\alpha_2)}{C_1(\alpha_1)}\right) \cdot \left(\frac{L_2}{L_1}\right) \cdot \left(\frac{W_2 + H}{W_1 + H}\right)^2 \cdot \left(\frac{W_1}{W_2}\right)^3 > 1. \qquad \text{Eqn (3)}$$

Note that this final expression does not contain any fluid velocity term, implying that a properly designed trap will work for all velocities in the laminar flow regime.

Optical-Based Microbubble Retrieval System

In Tan's microfluidic trap device, once all of the traps are occupied, the main flow will be redirected to the loop channels. Subsequent particles, not being able to enter occupied traps, will follow the main flow out of the device. Taking advantage of this characteristic Tan retrieved a trapped particle from the array by displacing it back into the main flow using microbubbles. Tan used a simple optical-based method to create microbubbles without any need for circuits and connections.

FIG. 5B is a diagram illustrating a release mechanism using a microbubble. The formed bubble displaces the trapped particle from the trap into the main flow. The particle is then carried by the main flow out of the device. Aluminum patterns, functioning as heaters, are located near the narrowed region of the microfluidic traps. When an infrared (IR) laser is focused onto the aluminum pattern, localized heating results in bubble formation and the expanding bubble displaces the immobilized particle from the microfluidic trap into the main flow. The displaced particle is then carried by the flow out of the device where it can be collected. The size of the bubble can be controlled by varying the laser power and duration of the applied laser.

The schematic of the Tan system is depicted in FIG. 5C. The device is mounted onto an inverted microscope with an automatic XY stage, which is controlled with a manipulator joystick. Other controllers regulate the intensity and duration of the laser, which is focused through the objective lens. The infusion system (pumps), laser system, and manipulation system can all be controlled by a computer, allowing total automation of the system in the future.

Tan indicated that based on experience, H should be set to $\Phi_p < H < 1.4 \Phi_p$ for the microfluidic trap to achieve one-bead-to-one trap. Tan's device is designed to trap particles of a specific size, and worked successfully with beads having a coefficient of variation of about 4%. One hundred microbeads can be arrayed in less than 20 s.

To demonstrate the individual addressability of the bead microarray, and the ease of operation of the trap-and-release device, beads were arrayed and subsequently selected beads were released to form patterned lines. This entire procedure was accomplished within a few minutes. Tan indicated that one characteristic of this device revealed by the demonstration is that it is necessary to release the beads in a predetermined order, from the upstream to the downstream of the flow, during retrieval of multiple beads from the array. In this case, beads were released sequentially from left to right. Failure to follow this order would result in released beads re-entering vacant traps farther downstream.

However, as presently contemplated, if one is only interested in releasing a particular bead for further use, there would be no need to use the above release sequence. One could release the bead of interest, and use it in further analysis. Thereafter, one could use the upstream to downstream release sequence to empty the traps to make the device ready for another bead trap and release sequence as needed.

Silicon Micropillar Fabrication

Silicon micropillar fabrication has been described in M. D. Henry, et al., "Alumina etch masks for fabrication of high-aspect-ratio silicon micropillars and nanopillars," Nanotechnology 20 (2009) 255305. Alumina offers substantially increased mask selectivity with little addition to fabrication complexity or specialized equipment. A 26 nm film permits ultrahigh resolution pattern transfer while providing an effective mask for etches greater than 100 µm, making alumina a suitable mask for next-generation electronics, photonics, MEMs, THz, and fluidic devices.

Fabrication on both the microscale and the nanoscale is performed using standard photo and electron beam lithographic techniques. The micropillars are photolithographically defined in Clarion AZ 5214 E photoresist (PR) spun on silicon with a 1.6 µm thickness. Following the ultraviolet 350 nm exposure, the patterns are developed using MF 322 developer. In one embodiment, a pattern generated to show the capability of the etching procedure consists of four arrays of hexagonally-packed pillars with diameters 5, 10, 20, and 50 µm. The spacing between pillars is equal to the pillar diameter. Similarly for the nanometer sized pillars, PMMA950 A 2 is spun to a thickness of approximately 75 nm and exposed via a 100 kV electron beam. The PMMA is developed using a 1:3 mixture of methyl-isobutyl-ketone to isopropanol. The nanopillars are arranged in hexagonally packed arrays where the separation between pillars is equal to twice the diameter of the pillar. The larger separation in the nanopillar case prevents the over-development and subsequent widening of the disks due to proximity error while writing with the electron beam.

Aluminum oxide is then deposited on the patterned silicon with a TES 1800 DC magnetron sputter system, using a 99.995% aluminum target and a 5:1 mixture of argon to oxygen as the process gas. This ratio of gases allows for the aluminum to be sputtered without poisoning the target while still deposits a stoichiometric aluminum oxide. At 400 W DC power, this process deposited alumina at an approximate rate of 10 nm min$^{-1}$. Liftoff is carried out in acetone for the micron scale and a mixture of acetone and dichloromethane for the nanoscale pattern. Unlike metal etch masks which are ductile, the brittle alumina fractures as the acetone swells the resist, enabling the ease of liftoff and allowing for a more faithful feature transfer than metal liftoff or wet etching.

Etching is performed using Oxford Instrument's PlasmaLab System100 ICP-RIE 380 s. Two different fluorinated etch chemistries are utilized to test the chemical and mechanical resiliency of the etch mask: a $SF_6/O_2$ cryogenic etch, which is more chemical in nature and the Pseudo-Bosch ($SF_6/C_4F_8$) etch, which involves more physical milling than the cryogenic etch. Both etch chemistries utilize a simultaneous etching and passivation technique, allowing for precise control over the etch anisotropy. Details of the etches may be found in deBoer M J, Gardeniers J G E, Jansen H V, Smulders E, Gilde M J, Roelofs G, Sasserath J N and Elwenspoek M 2002 *J. Microelectromech. Syst.* 1 385 and in Welch C C, Goodyear A L, Wahlbrink T, Lemme M C and Mollenhauer T 2006 *Microelectron. Eng.* 83 1170-3. We performed an optimized cryogenic etch for the creation of micropillars and an optimized Pseudo-Bosch for nanopillars.

Cryogenic etching achieves etch rates of several microns per minute, facilitating the fabrication of large structures. The etch produces pillars with aspect ratios greater than 12 and etch depths up to 150 μm. An inductively coupled plasma (ICP) power of 900 W combined with a RIE power of 3-9 W established a strong chemical etch with minimal milling. A 10 to 1 ratio of $SF_6$ to $O_2$ balances the etch and passivation rates to provide sidewall angles of 88°-91°.

For each set of 5-50 μm diameter pillars, etch depths between 50 and 160 μm are achieved by varying the etch time in the range of 40 to 160 minutes. Surface roughness is typically a few hundred nanometers but occasional micron sized striations occur due to the beginnings of mask erosion. The micropillars/nanopillars are imaged and measured using a FEI Quanta and Sirion scanning electron microscope.

Principle of Operation

Figure 6:
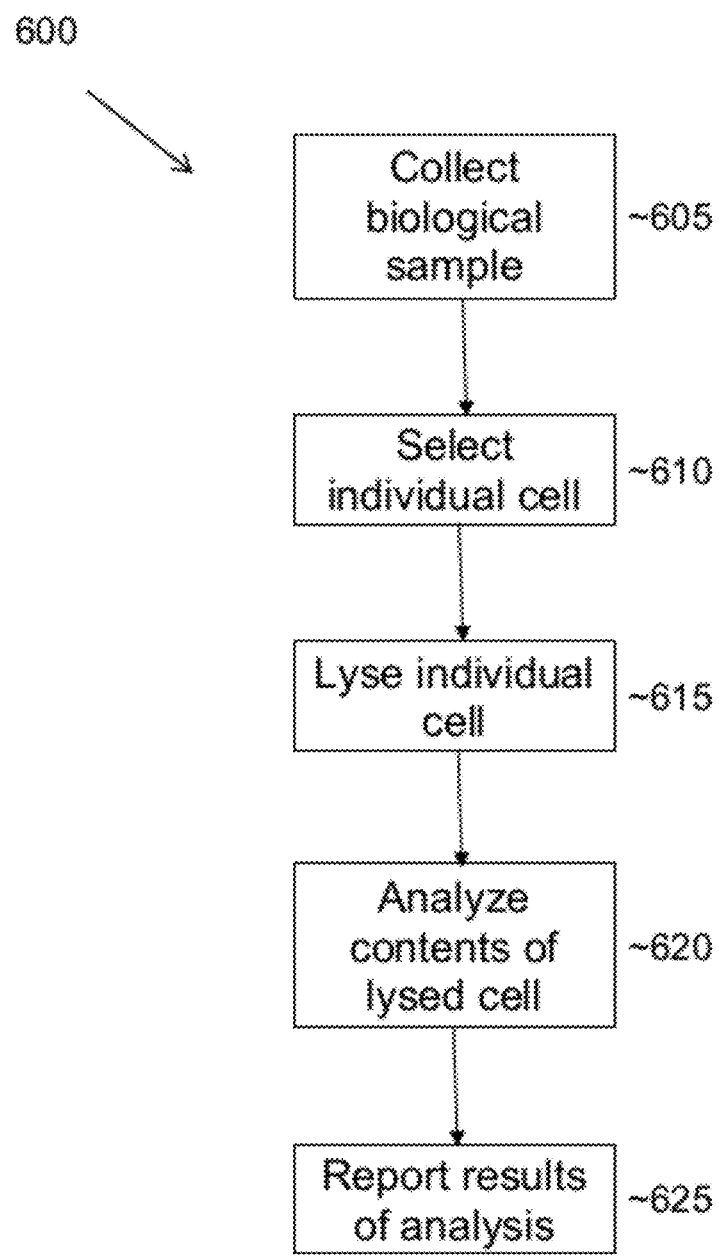
FIG. 6 is a schematic flow diagram of a method of lysing a single cell and using its contents according to principles of the invention.

FIG. 6 is a schematic flow diagram of a method of lysing a single cell and using its contents according to principles of the invention. As illustrated in FIG. 6, a biological sample of interest is collected, which is represented by step 605. The sample can in general be of any biological origin, including one or more cells from a mammal or other multicellular animal or plant, a sample of a single cell animal or plant, for example a bacterium or an egg cell, or some other biological material such as a spore or a virus.

At step 610, one selects an individual cell of interest. This step can be accomplished in any convenient manner, including selection of a cell by manual means, by use of a trap and release structure such as that of FIG. 5A, FIG. 5B or FIG. 5C, or another apparatus, for example that shown in FIG. 7. The identification of the cell of interest can include the use of chemicals, such as fluorescent dyes, stains or fluorescent proteins, and can include the use of optical methods such as microscopy and Raman spectroscopy. In some embodiments, a cell of interest may be attached to a microbead in order to assure that the cell will be trapped in a trap and release apparatus designed to operate with particles such as beads having a well-defined dimension.

Having identified and selected a single cell in step 610, the cell is then provided to a single cell lysing device including a stress raiser, such as shown in FIG. 4 (with or without a microblade). The cell of interest is then lysed as indicated in step 615.

In step 620, the lysate (or contents of the lysed cell of interest) is analyzed. Any convenient analysis method can be used, including replication of biological material, for example with PCR methods, chemical analysis, analysis using materials that interact with the lysate or with products generated from or by the lysate so as to provide analytical information about the lysate and/or the lysed cell.

In step 625, the results of the analysis are reported, which can include any or all of storing the results of the analysis, displaying the results of the analysis to a user, and/or transmitting the results of the analysis to another user or machine for further processing.

Alternative Trap and Release Device

Figure 7:
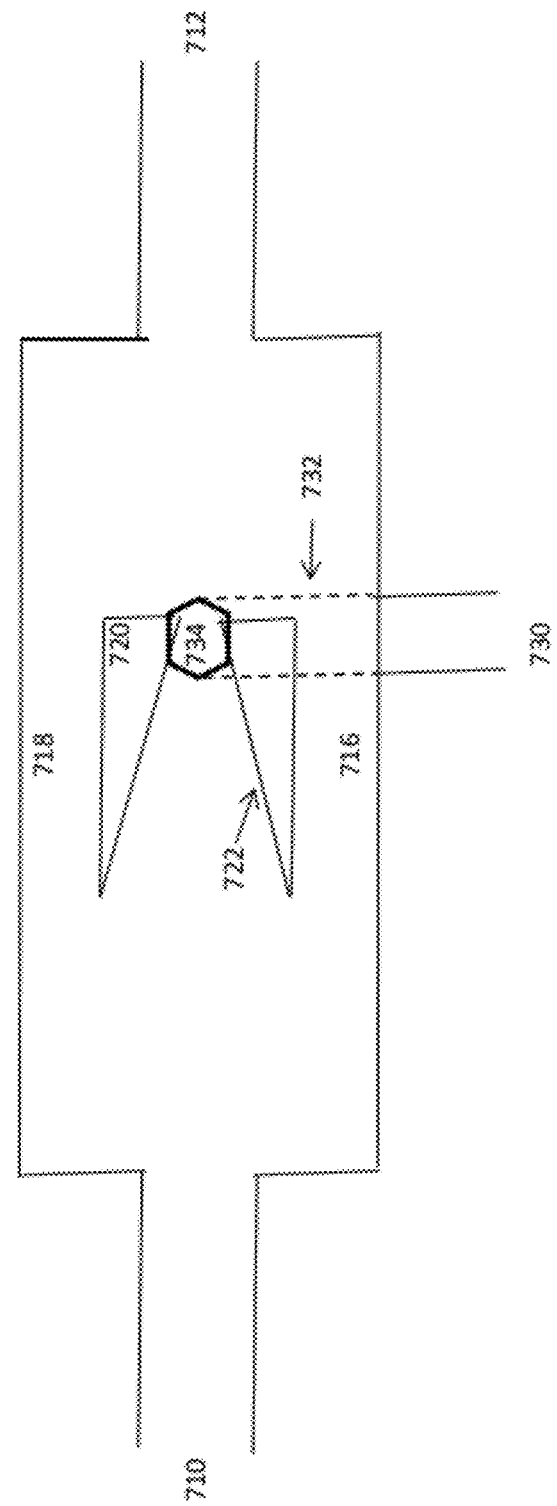
FIG. 7 is a schematic diagram in plan view of an alternative embodiment of a microfluidic trap and release apparatus.

FIG. 7 is a schematic diagram in plan view of an alternative embodiment of a microfluidic trap and release apparatus. In FIG. 7, an input port 710 is provided through which material of interest can flow into the microfluidic trap and release apparatus. An outlet port 712 is also provided to allow flow to occur through the device. In the plan view of FIG. 7, the input to output flow is from left to right. Valves (not shown) such as valves 410 and 412 of FIG. 4 are provided to control the flow through the device. As shown in plan view, there is a "straight through" path between trap elements 720 and 722 that form a trap for a particle, and there are "bypass" flow paths 716 and 718 around the trap elements 720 and 722 to allow fluid to pass through the device when a particle is trapped between trap elements 720 and 722. In the device of FIG. 7, an alternative release structure is provided. Aperture 734, shown as a hexagon, is an aperture situated between elements 720 and 722, but oriented in a plane normal to the plane of flow of the input and output. That is, aperture 734 is oriented to allow flow perpendicular to the plane of drawing of FIG. 7. Aperture 734 is connected to a valve 730 by a tubulation 732, which can be in a plane above or below the plane of flow from port 710 to port 712. Normally, valve 730 is closed, so there in no net flow through tabulation 732.

In a first mode of operation to collect a trapped cell, when a cell of interest is trapped between trap elements 720 and 722, one can close the valve that allows additional material to, flow into port 710, and can open valve 730 to apply increased pressure to aperture 734 via tubulation 732 to dislodge the trapped cell, and allow it to flow out of the cell via port 712 (or via another port provided specifically to collect the cell of interest).

In a second mode of operation, when a cell of interest is trapped between trap elements 720 and 722, one can close the valve that allows material to flow out of port 712, and can open valve 730 to apply reduced pressure (e.g., suction) to aperture 734 via tabulation 732, so that flow entering port 710 can dislodge the trapped cell, and allow it to flow out of the cell via aperture 734 and tubulation 732.

Once a cell of interest has been trapped and collected using the device of FIG. 7, it can be individually lysed using the apparatus of FIG. 4 (e.g., the device of FIG. 7 operates as the source 402 of biological material shown in FIG. 4).

U.S. Pat. No. 8,002,235, assigned to the same assignee as the present application, discusses valves for microfluidic systems that can be used to construct the apparatus contemplated herein.

DEFINITIONS

Unless otherwise explicitly recited herein, any reference to an electronic signal or an electromagnetic signal (or their equivalents) is to be understood as referring to a non-volatile electronic signal or a non-volatile electromagnetic signal.

Recording the results from an operation or data acquisition, such as for example, recording results of an analysis, is understood to mean and is defined herein as writing output data in a non-transitory manner to a storage element, to a machine-readable storage medium, or to a storage device. Non-transitory machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/SD adapter) that accommodate and read from and/or write to the storage media. Unless otherwise explicitly recited, any reference herein to "record" or "recording" is understood to refer to a non-transitory record or a non-transitory recording.

As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes. Recording image data for later use (e.g., writing an image to memory or to digital memory) can be performed to enable the use of the recorded information as output, as data for display to a user, or as data to be made available for later use. Such digital memory elements or chips can be standalone memory devices, or can be incorporated within a device of interest. "Writing output data" or "writing an image to memory" is defined herein as including writing transformed data to registers within a microcomputer.

"Microcomputer" is defined herein as synonymous with microprocessor, microcontroller, and digital signal processor ("DSP").

General purpose programmable computers useful for controlling instrumentation, recording signals and analyzing signals or data according to the present description can be any of a personal computer (PC), a microprocessor based computer, a portable computer, or other type of processing device. The general purpose programmable computer typically comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of UNIX, or of Linux. Computational results obtained in the operation of the general purpose computer can be stored for later use, and/or can be displayed to a user. At the very least, each microprocessor-based general purpose computer has registers that store the results of each computational step within the microprocessor, which results are then commonly stored in cache memory for later use.

Many functions of electrical and electronic apparatus can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware and software for another implementation of the equivalent functionality using a different one of hardware, firmware and software.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, or publication identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. A mechanical cell lysing apparatus with single cell resolution, comprising:
an inlet port having an inlet valve configured to permit a source of biological material having a cell of interest to enter said mechanical single cell lysing apparatus;
a drain port having a drain valve configured to permit said source of biological material to exit said mechanical single cell lysing apparatus;
a trap structure configured to trap said cell of interest in said single cell lysing apparatus; the trap structure having an inlet and an outlet;
a stress raiser configured to raise a mechanical stress on a membrane of said cell of interest trapped in said trap structure, wherein the stress raiser is positioned within the outlet of the trap structure;
a pressure application element having a pressure application valve configured to apply a pressure to said cell of interest, said pressure application element configured to cooperate with said stress raiser to provide sufficient mechanical stress to lyse said cell of interest trapped in said trap structure; and
an outlet port having an outlet valve configured to allow components of said lysed cell of interest to exit said mechanical single cell lysing apparatus to be analyzed.

2. The mechanical cell lysing apparatus with single cell resolution of claim 1, wherein said stress raiser is a nanoblade.

3. The mechanical cell lysing apparatus with single cell resolution of claim 1, wherein said pressure application element is a manually operated pressure application element.

4. The mechanical cell lysing apparatus with single cell resolution of claim 1, wherein said pressure application element is an electrically operated pressure application element.

5. The mechanical cell lysing apparatus with single cell resolution of claim 4, wherein said electrically operated pressure application element is configured to be controlled by a computer.

6. The mechanical cell lysing apparatus with single cell resolution of claim 1, wherein a flow condition of said biological material through said inlet port and said drain port is controlled by said inlet valve and said drain valve, and wherein a flow of the components of said mechanically lysed cell through said outlet port is controlled by the outlet valve.

7. The mechanical cell lysing apparatus with single cell resolution of claim 1, wherein said apparatus comprises a selected one of silicon, glass, quartz, polymer and metal material.

8. The mechanical cell lysing apparatus with single cell resolution of claim 1, wherein said apparatus is configured as a handheld device.

9. A mechanical cell lysing method with single cell resolution, comprising the steps of:
providing a mechanical cell lysing apparatus with single cell resolution, including
an inlet port having an inlet valve configured to permit a source of biological material having a cell of interest to enter said mechanical single cell lysing apparatus,
a drain port having a drain valve configured to permit said source of biological material to exit said mechanical single cell lysing apparatus,
a trap structure configured to trap said cell of interest in said single cell lysing apparatus, the trap structure having an inlet and an outlet,
a stress raiser configured to raise a mechanical stress on a membrane of said cell of interest trapped in said trap structure, wherein the stress raiser is positioned within the outlet of the trap structure,
a pressure application element having a pressure application valve configured to apply a pressure to said cell of interest, said pressure application element configured to cooperate with said stress raiser to provide sufficient mechanical stress to lyse said cell of interest trapped in said trap structure, and
an outlet port having an outlet valve configured to allow components of said lysed cell of interest to exit said mechanical single cell lysing apparatus to be analyzed;
providing a biological material of interest;
selecting a single cell to be lysed;
introducing said single cell to be lysed into said mechanical single cell lysing apparatus by opening and then closing said inlet valve and said drain valve;
applying sufficient pressure to mechanically lyse said single cell, including opening said pressure application valve and said outlet valve; and
providing components of said mechanically lysed single cell for analysis.

10. The mechanical cell lysing method with single cell resolution of claim 9, wherein said step of applying sufficient pressure to mechanically lyse said single cell is performed manually.

11. The mechanical cell lysing method with single cell resolution of claim 9, wherein said step of applying sufficient pressure to mechanically lyse said single cell is performed electrically.

12. The mechanical cell lysing method with single cell resolution of claim 9, wherein said step of selecting a single cell to be lysed is performed using a trap and release apparatus.

13. The mechanical cell lysing method with single cell resolution of claim 9, wherein said step of selecting a single cell to be lysed is performed using a visual method of identification of said cell.

14. The mechanical cell lysing method with single cell resolution of claim 13, wherein said visual method of identification of said cell comprises a method selected from the methods including staining said cell, fluorescence in situ hybridization (FISH), fluorescent protein transfection, and Raman spectroscopy.

15. The mechanical cell lysing method with single cell resolution of claim 9, wherein said step of selecting a single cell to be lysed is performed manually.

16. The mechanical cell lysing method with single cell resolution of claim 9, further comprising the steps of analyzing a component of said lysed cell and reporting a result of said analysis.

17. The mechanical cell lysing apparatus with single cell resolution of claim 1, wherein the trap structure is a V-shaped groove structure having a center opening smaller than the cell of interest.

18. The mechanical cell lysing method with single cell resolution of claim 9, wherein the step of providing a mechanical cell lysing apparatus comprising a trap structure includes providing a V-shaped groove structure having a center opening smaller than the cell of interest.

19. The mechanical cell lysing method with single cell resolution of claim 9, wherein the step of providing a mechanical cell lysing apparatus comprising a trap structure includes providing a nanoblade as a stress raiser.

20. The mechanical cell lysing apparatus with single cell resolution of claim 2, wherein the trap structure is formed from at least two micropillars or at least two nanopillars.

* * * * *